(12) United States Patent
Biscotti

(10) Patent No.: US 7,500,562 B2
(45) Date of Patent: Mar. 10, 2009

(54) NEEDLE ASSEMBLY HOLDING TRAY

(75) Inventor: Anthony Biscotti, Acton, MA (US)

(73) Assignee: Nuclear Consultant Group, Inc., Acton, MA (US)

( * ) Notice: Subject to any disclaimer, the term of this patent is extended or adjusted under 35 U.S.C. 154(b) by 561 days.

(21) Appl. No.: 11/243,245

(22) Filed: Oct. 4, 2005

(65) Prior Publication Data

US 2006/0102502 A1     May 18, 2006

Related U.S. Application Data

(60) Provisional application No. 60/615,789, filed on Oct. 4, 2004.

(51) Int. Cl.
    *B65D 85/28*      (2006.01)

(52) U.S. Cl. ........................... 206/380; 206/382

(58) Field of Classification Search ............... 206/380, 206/381, 382, 574, 45.24, 45.2, 762; 250/584, 250/484.4
See application file for complete search history.

(56) References Cited

U.S. PATENT DOCUMENTS

| | | | | |
|---|---|---|---|---|
| 2,713,937 A | * | 7/1955 | Schneider | 206/380 |
| 2,817,434 A | * | 12/1957 | Schmetz et al. | 206/380 |
| 3,227,265 A | * | 1/1966 | Schneider | 206/382 |
| 4,210,239 A | * | 7/1980 | Takahashi | 206/760 |
| 4,243,141 A | * | 1/1981 | Takahashi | 206/380 |
| 5,460,267 A | * | 10/1995 | Schiffer | 206/380 |
| 5,853,087 A | * | 12/1998 | Sos et al. | 206/380 |
| 6,619,476 B2 | * | 9/2003 | Hoch et al. | 206/380 |
| 6,949,064 B2 | * | 9/2005 | Lowery et al. | 600/7 |
| 2003/0127349 A1 | * | 7/2003 | Faller et al. | 206/380 |
| 2005/0191207 A1 | * | 9/2005 | Terwilliger et al. | 422/28 |

* cited by examiner

*Primary Examiner*—David T Fidei
(74) *Attorney, Agent, or Firm*—Brian M. Dingman; Mirick, O'Connell, DeMallie & Lougee, LLP

(57) ABSTRACT

The needle assembly tray of the invention generally comprises a base tray having an upper portion, a lower portion, and a groove, that enables the base tray to be bent, a plurality of needle channels in the lower portion, substantially conical shaped openings leading into the needle channels, and a security strip for maintaining needles securely in the needle channels when the base tray is bent, and a lid for the base tray. The tray is adapted to lay flat during shipping but, in use, the upper half of the tray is bent away from the upper half of the assembly to expose the assembly and create a stand on which to prop the tray.

12 Claims, 3 Drawing Sheets

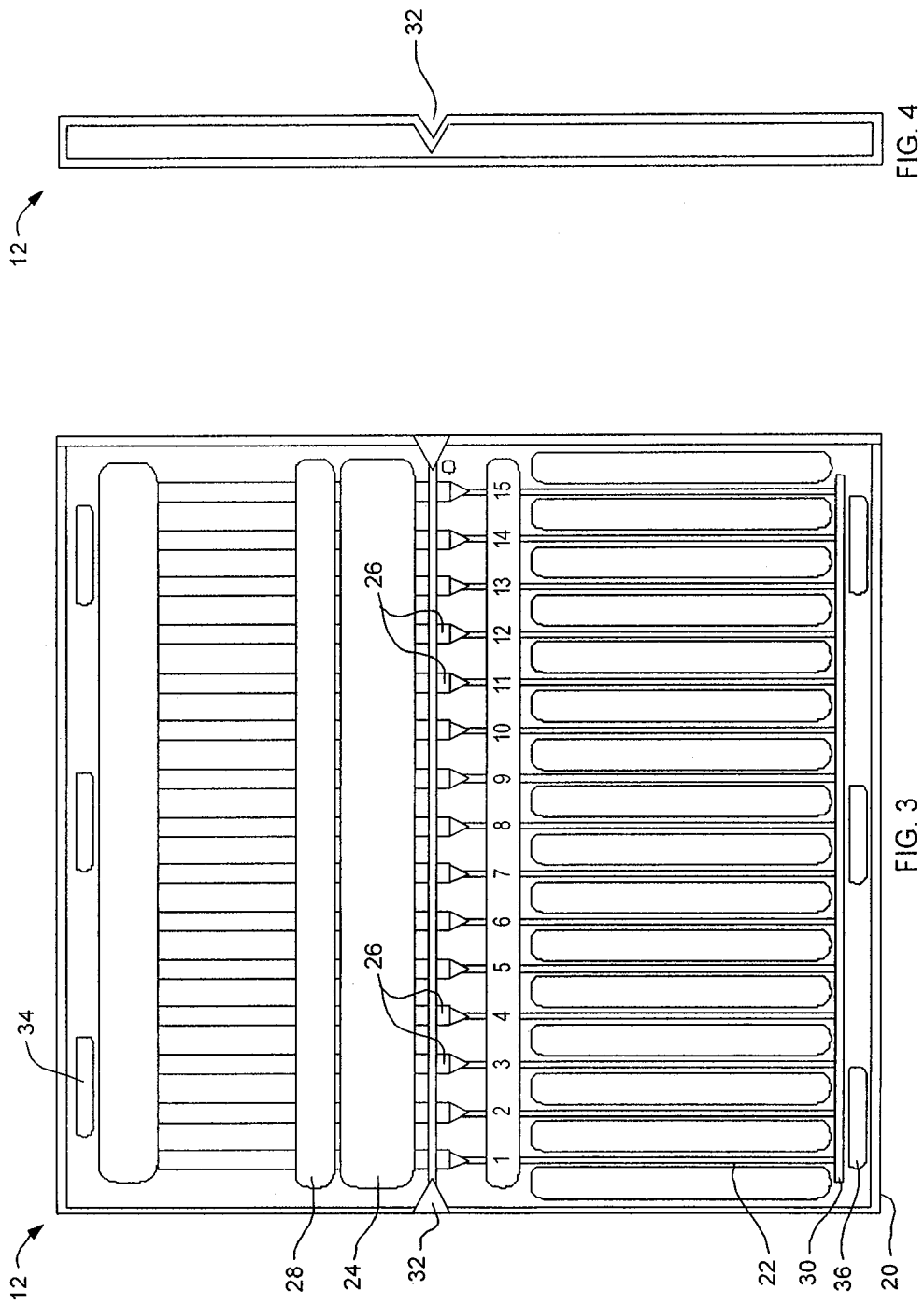

NEEDLE ASSEMBLY HOLDING TRAY

CROSS-REFERENCE

This is a continuation-in-part of U.S. Provisional Patent Application Ser. No. 60/615,789 filed on Oct. 4, 2004.

FIELD OF THE INVENTION

This invention relates to a brachytherapy needles and more specifically to trays for packaging and holding the needles and methods for using such trays.

BACKGROUND OF THE INVENTION

Generally, needle trays used in the transport of brachytherapy needles pre-loaded with brachytherapy radioactive "seeds" are known. However, the trays currently available on the market either poorly support the delicate pre-loaded needles inside or are difficult to work with for both the individual inserting the needle/stylet into these trays and the person removing them from the tray.

Additionally, the current designs often times create a barrier to performing a necessary piece of quality control called a radiograph. When performing a radiograph, a piece of x-ray film, properly encased to prevent exposure to light, is laid over the lower half of the loaded needles in the tray. If the tray is too thick it will not allow the x-ray film to almost touch the shaft of the loaded needles as the radiograph procedure is being performed. This results in a poorly defined image of the seed placement in the series of pre-loaded needles. A poorly defined image makes it difficult to determine whether the seeds loaded inside the needles are spaced according to the "pre-plan" loading pattern for the given case.

Further problems result from the current designs of the channel in which the loaded needle/stylet combination is inserted. Current designs typically require the needle to be "woven" through a series of small slits in the tray to secure the series of needles in the proper order in the tray. Because each tray will contain an average of about 30 needles and about 100 radioactive seeds, the longer it takes the user to get the needles into the tray, the more radioactive exposure the user will receive, creating a more dangerous work environment.

Other tray designs require the operator to send the needle down a channel. When the channel is too big, this negatively affects the quality of the radiograph. When the channel is too small, then the target into which the operator must thread the needle is too small.

In addition, all available trays on the market lay flat or are rolled up during shipping and when in the operating room, at implant time, are laid flat. A flat tray makes assess to the needles difficult because the needle is against the tray on one side leaving little room for the users fingers to grasp the small needle hub. Complicating the matter further is the fact that the needles are aliened close to the next needle leaving little room for fingers.

SUMMARY OF THE INVENTION

It is therefore a primary object of this invention to provide a tray system that facilitates loading the needles into the tray while retaining the ability to create quality radiographs.

It is a further object of the invention to provide a tray system that enables the end user to readily remove the needles from the tray while retaining the rigidity of the tray to adequately protect the needles during shipping and handling.

It is a further object of the invention to provide a needle assembly tray that positions the needles closer to the backside of the tray so that radiographs of the loaded needles taken from the backside of the tray are substantially clearer.

The tray of the invention is an advance for packaging and holding brachytherapy needles with radioactive seeds. The tray of the invention is the result of efforts to develop an improved tray system that addresses the problems associated with previous designs.

A preferred embodiment of the needle assembly tray of the invention generally comprises: a base tray having an upper portion, a lower portion, and a means for bending the base tray located between the upper and lower portions; wherein the base tray comprises, a plurality of needle channels in the lower portion, substantially conical shaped openings leading into the needle channels, and a means for maintaining the needles securely in the needle channels when the base tray is bent; and a lid for the base tray.

The upper portion of the base tray preferably has a forward edge and the lower portion of the base tray has a rearward edge, and the lid preferably has a means for holding the forward and rearward edges of the base tray in place when the base tray is bent. Such means for holding the forward and rearward edges preferably comprises ridges or other such raised areas or, alternatively, grooves.

The base tray may further comprise a clip recess for allowing needles with clips to be loaded and stored in the tray. The means for maintaining the needles securely in the needle channels, preferably comprises a security strip located proximate the rearward edge.

The lid also may comprise an upper lid and a lower lid that can be separately attached to and removed from the base tray, wherein the upper lid is adapted to cover the upper portion of the base tray and the lower lid is adapted to cover the lower portion of the base tray.

The base tray may still further comprise a means for securing needles in the upper portion of the base tray, wherein the means for securing preferably comprises a security recess in the upper portion and a resilient strip provided in the security recess so that when the lid is fixed to the base tray, the needles are fixed in place between the lid and resilient strip.

The method of the invention for using the needle assembly tray of the invention generally comprises the steps of: providing a needle assembly tray comprising, a base tray having an upper portion, a lower portion, and a means for bending the base tray located between the upper and lower portions; wherein the base tray comprises, a plurality of needle channels in the lower portion, and substantially conical shaped openings leading into the needle channels into which one or more needles have been inserted; and a lid attached to the base tray; wherein the upper portion of the base tray has a forward edge and the lower portion of the base tray has a rearward edge, and wherein the lid comprises a means for holding the forward and rearward edges of the base tray in place when the base tray is bent; removing the lid from the base tray; bending the based tray along the means for bending; and resting the forward and rearward edges of the base tray on the lid.

The method for using a loaded needle assembly tray of the invention generally comprises the steps of: providing a needle assembly tray comprising: a base tray having a backside, wherein said base tray comprises, a plurality of brachytherapy needles loaded with seeds located in needle channels having a bottom inside surface in the lower portion, a means for snugly securing the needles against the bottom inside surface of the needle channel and a lid for the base tray; turning the needle assembly tray over so that the backside of the tray faces upwards; placing x-ray film on the backside of the tray; radiographing the needles in the needle assembly tray.

Needles typically have a stylet that, when the base tray is bent, the stylet should be generally positioned in the upper portion of the base tray. In such instances of the method, the base tray preferably further comprises a means for bending the base tray located between the upper and lower portions and a means for maintaining the needles securely in the needle channels when the base tray is bent, and the method then further comprises the steps of, bending the base tray so that the stylets extend outward from the base tray so that they may be readily grasped and removed; and resting the forward and rearward edges of the base tray on the lid.

BRIEF DESCRIPTION OF THE DRAWINGS

Other objects, features and advantages will occur to those skilled in the art from the following description of the preferred embodiments and the accompanying drawings in which:

FIG. 3 is a perspective view of the preferred embodiment of the tray of the invention shown with the upper and lower lids.

FIG. 4 is a perspective view of the embodiment shown in FIG. 4 in an open folded position.

DETAILED DESCRIPTION OF THE PREFERRED EMBODIMENTS AND METHODS

The tray of the invention decreases the likelihood of damage to pre-loaded needles during transport of any type while also making it properly suited to perform the necessary quality control procedure of radio graphing the seed placement in the needles. The tray of the invention also provides a more ergonomically friendly design for the individual placing the needles into the tray and the end user removing the needles from the tray for implanting.

The objects of the invention are in part achieved using a funnel shaped design at the top of the channel with a narrow channel towards the bottom. A stout outer frame section is used in the tray to provide the necessary rigidity in the tray to protect the needles during shipping and handling.

As noted, trays on the market today lay flat or are rolled up during shipping and when in the operating room, at implant time, are laid flat. A flat tray makes access to the needles difficult because the needle is against the tray on one side leaving little room for the user's fingers to grasp the small needle hub. The tray of the invention remedies this problem. The tray of the invention lays flat during shipping but the upper half of the tray is able to fold (bend) away from the upper half of the needle/stylet assembly, thereby exposing the assembly and creating a stand on which to prop the tray to provide a better view of the tray of needles as it sits on the operating room cart and to provide ready access to the individual needles.

In addition, some of the needles currently on the market utilize a clip to attach the stylet to the needle hub to prevent the stylet from sliding out of the needle during transport. The clips of various styles and sizes must fit into the tray, yet the trays currently on the market do not typically accommodate the different styles and shapes of the clips on the market. Additionally, the clips create a mess to cleanup after they have been removed from the needles. The tray of the invention solves this problem by eliminating the need for the clip altogether. The preferred embodiment of the tray of the invention has a upper foam ridge on which the stylet rests and an upper cover that, when fitted to the tray, "sandwiches" the stylet between the upper tray cover and the foam strip on the bottom base tray. The strip may be made from any suitably resilient material. Eliminating the clips allows the assembler of the loaded needles, and the end user who would normally have to remove the clip prior to the use of the needle, to work faster. This decreases the total potential exposure received from the radioactivity.

Figure 1:
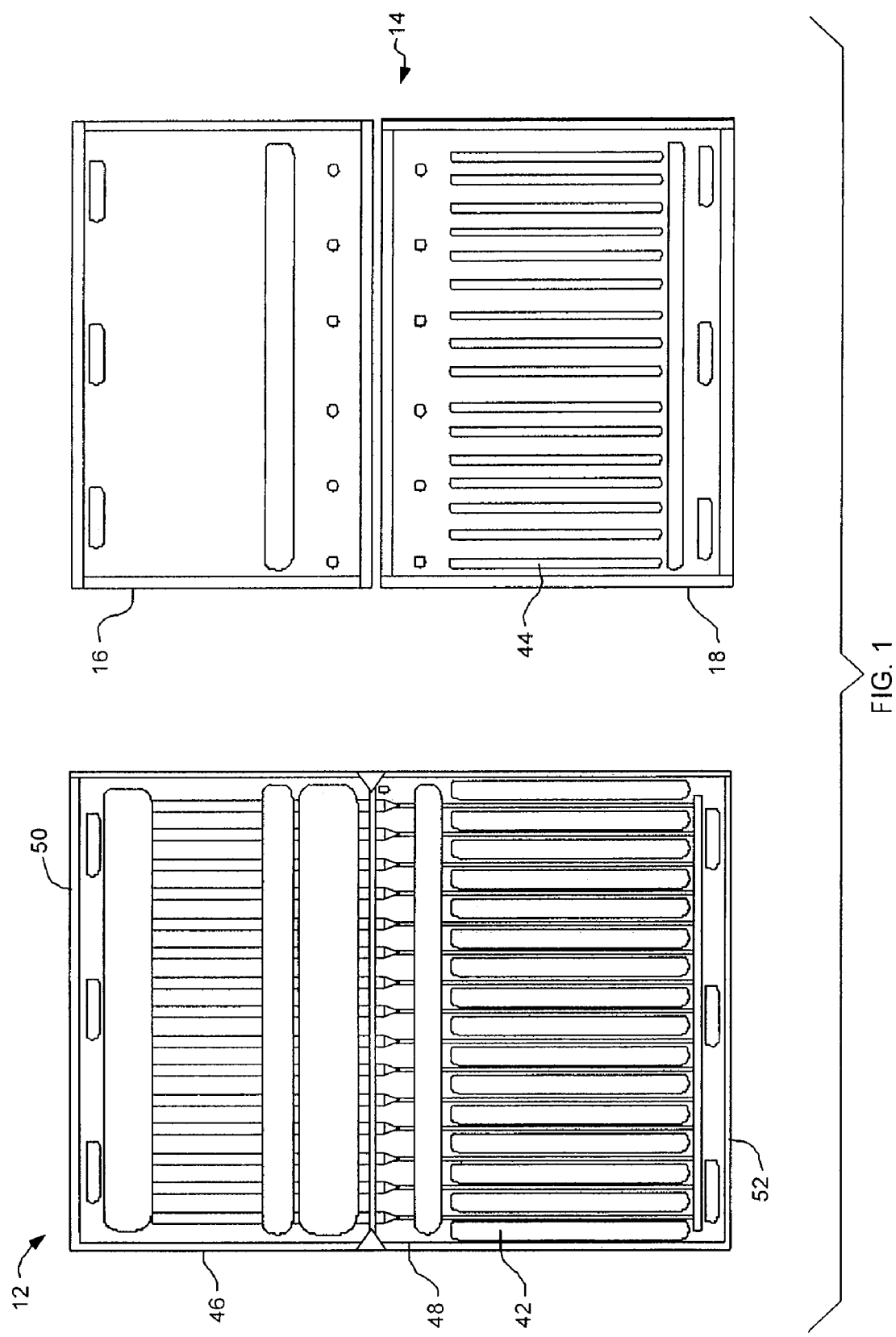
FIG. 1 is a side view of the preferred embodiment of the base tray of the invention.
Figure 2:
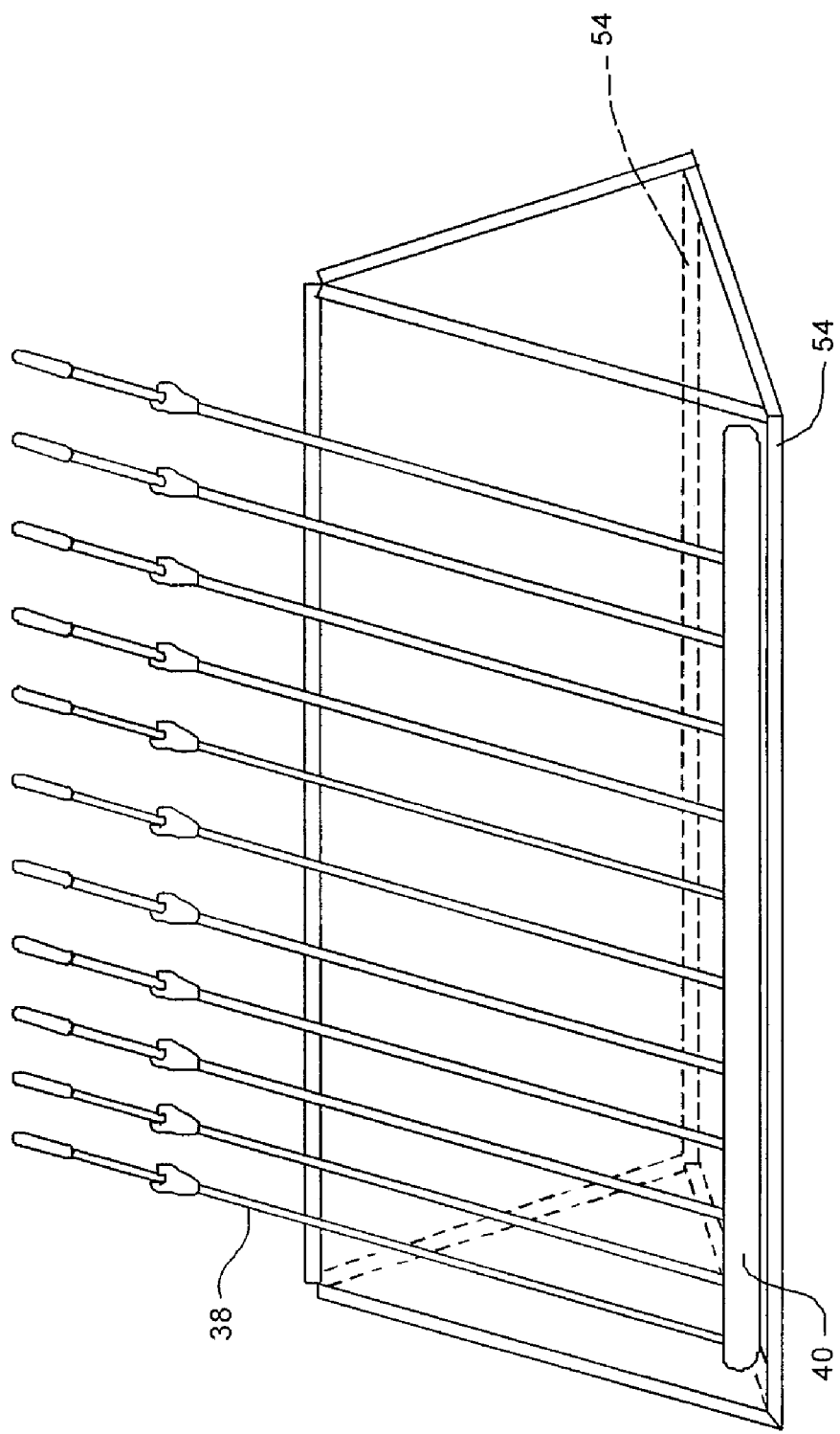
FIG. 2 is a top view of the base tray of the embodiment shown in FIG. 1.

The preferred embodiment of the invention is generally shown and referred to in FIG. 1 through as tray 10. In FIG. 1, tray 10 is shown with the base 12 and lid 14 separate and laying side-by-side. Lid 14 is generally divided into two sections upper lid 16 and lower lid 18. The upper lid and lower lids may be separately attached to and removed from the base tray Base 12 is adapted to bend along groove 32, as shown in FIG. 2, and to be placed on, and held in place by, upper lid 16. When base 12 is bent, upper portion 46 bends backward away from the stylets and the lower portion 48 remains substantially upright to support the needles 38 in an upright position for easy access. To secure base 12 in the bent position, the forward edge 50 of base 12 is placed against the forward portion of lip or ridge 54 of upper lid 16 and the rearward edge 52 of base 12 is placed against the rearward lip or ridge 54 of upper lid 16. Lid 14 may also be provided with grooves into which the edges of the bent base 12 may be inserted to hold the tray in place. Other means for holding base 12 is place include, but are not limited to, detents, snaps, adhesive strips, and virtually any type of openings with corresponding protrusions.

Base 12 is shown in more detail in FIG. 3. Base 12 generally comprises a reinforced outer frame 20 to provide stability and rigidity to the overall tray; channels 22, preferably having a depth of about 1 mm, to hold a needle shaft (not shown in FIG. 3); a large recessed area 24 (if desired) to accommodate grip clips (if desired) of varying shapes and sizes; funnels 26 to facilitate easy insertion of needles into holding channel 22; recessed channel 28 into which a foam strip fits and rests against the stylet of the needle (not shown in FIG. 3) to help secure the stylet in place when lid 14 is placed on top of base 12; channel 30 (shown in FIG. 3) into which a foam strip 40 (shown in FIG. 2) is fit to hold the needle tip in place; groove 32 running from across the width of base 12 to enable base 12 to fold in half so that the upper portion of base 12 folds away from the needle assembly; and pressure fit button holes 34 and 36 at the top and bottom of base 12 to attach and secure lid 14 to base 12. Groove 32 is shown in cross-section in FIG. 4. Channels 22 may be adapted to hold needles of any length. The preferred length for brachytherapy needles ranges from 21.5 cm to 22.5 cm. Recessed channel 28, together with the foam strip obviate the need for grip clips. Recess 24 may be provided in addition to channel 28 simply to accommodate such grip clips if desired.

Although the preferred embodiment shown in the Figures accommodates fifteen needles, the tray of the invention may be modified to store virtually any practical number of needles and compartments.

A plurality of strips 42, made from a resilient material such as foam, are preferably provided on base 12 between channels 22, and a corresponding plurality of ridges 44 are preferably provided on lower lid 18. When lid 14 is secured to base 12, strips 42 are friction fit against ridges 44 to secure the needles in channels 22. This tight friction fit causes the loaded needles to sit snugly against the floor of channels 22 which, in turn, facilitates much clearer radiographs or x-rays of the loaded needles. Once the needles are assembled in the tray and the lid snapped into place on the base tray, the tray can then be x-ray for quality assurance purposes to ensure that the seeds in the needles are properly loaded according to the "pre-plan" loading pattern for the given case. To achieve the improved radiograph, the entire tray is turned over and the x-ray film is laid on the backside of base tray 12 and the x-ray taken. Since the needles are held snugly against the backside of the base tray, the radiograph is substantially clearer than radiographs of previously available loaded trays.

As shown in FIG. 2, base 12 can be folded backwards along groove 32 and held in place by resting on grooves provided in lid 14 after lid 14 is laid flat on a table top. When base 12 is folded and secured in place on lid 14, needles 38 are in an exposed position. Foam 40 is left in place in groove 30 to hold the needle tips in place.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A needle assembly tray comprising:
    a base tray having an upper portion, a lower portion, and a means for bending said base tray located between said upper and lower portions; wherein said base tray comprises,
        a plurality of needle channels in said lower portion,
        substantially conical shaped openings leading into said needle channels, and
        a means for maintaining needles securely in said needle channels when said base tray is bent; and
    a lid for said base tray.

2. The needle assembly tray of claim 1 wherein said upper portion of said base tray has a forward edge and said lower portion of said base tray has a rearward edge, and wherein said lid comprises a means for holding said forward and rearward edges of said base tray in place when said base tray is bent.

3. The needle assembly tray of claim 2 wherein said means for holding said forward and rearward edges comprises ridges.

4. The needle assembly tray of claim 1, wherein said base tray further comprises a clip recess.

5. The needle assemble tray of claim 1, wherein said means for maintaining said needles securely in said needle channels comprises a security strip proximate said rearward edge.

6. The needle assembly tray of claim 1, wherein said lid comprises an upper lid and a lower lid that can be separately attached to and removed from said base tray.

7. The needle assembly tray of claim 6, wherein said upper lid is adapted to cover said upper portion of said base tray and said lower lid is adapted to cover said lower portion of said base tray.

8. The needle assembly tray of claim 1, further comprising a means for securing stylets in said upper portion of said base tray.

9. The needle assembly tray of claim 8, wherein said means for securing comprises a security recess in said upper portion and a resilient strip provided in said security recess so that when said lid is fixed to said base tray, the stylets are fixed in place between said lid and resilient strip.

10. A method for using a needle assembly tray comprising the steps of:
    providing a needle assembly tray comprising:
        a base tray having an upper portion, a lower portion, and a means for bending said base tray located between said upper and lower portions; wherein said base tray comprises,
            a plurality of needle channels in said lower portion, and
            substantially conical shaped openings leading into said needle channels into which one or more needles have been inserted; and
        a lid attached to said base tray;
        wherein said upper portion of said base tray has a forward edge and said lower portion of said base tray has a rearward edge, and wherein said lid comprises a means for holding said forward and rearward edges of said base tray in place when said base tray is bent;
    removing said lid from said base tray;
    bending said based tray along said means for bending; and
    resting said forward and rearward edges of said base tray on said lid.

11. A method for using a loaded needle assembly tray comprising the steps of:
    providing a needle assembly tray comprising,
        a base tray having a backside, wherein said base tray comprises,
            a plurality of brachytherapy needles loaded with seeds located in needle channels having a bottom inside surface in said lower portion,
            a means for snugly securing said needles against said bottom inside surface of said needle channel and
        a lid for said base tray;
    turning said needle assembly tray over so that said backside of said tray faces upwards;
    placing x-ray film on said backside of said tray; and
    radiographing said needles in said needle assembly tray.

12. The method of claim 11, wherein said needles have a stylet generally positioned in the upper portion of said base tray and wherein said base tray further comprises a means for bending said base tray located between said upper and lower portions and a means for maintaining said needles securely in said needle channels when said base tray is bent, and further comprising the steps of,
    bending said base tray so that said styletes extend outward from the base tray so that they may be readily grasped and removed; and
    resting said forward and rearward edges of said base tray on said lid.

* * * * *